United States Patent
Paradis

(10) Patent No.: US 11,679,059 B2
(45) Date of Patent: Jun. 20, 2023

(54) METHODS AND DEVICES TO IMPROVE THE EFFICACY OF MECHANICAL CARDIOPULMONARY RESUSCITATION BY CHANGING THE POSITION OF CHEST COMPRESSION

(71) Applicant: CPR Therapeutics, Inc., Putney, VT (US)

(72) Inventor: Norman Alan Paradis, Putney, VT (US)

(*) Notice: Subject to any disclaimer, the term of this patent is extended or adjusted under 35 U.S.C. 154(b) by 980 days.

(21) Appl. No.: 16/236,470

(22) Filed: Dec. 29, 2018

(65) Prior Publication Data

US 2019/0209428 A1 Jul. 11, 2019

Related U.S. Application Data

(60) Provisional application No. 62/612,398, filed on Dec. 30, 2017.

(51) Int. Cl.
*A61H 31/00* (2006.01)
*A61H 9/00* (2006.01)
(Continued)

(52) U.S. Cl.
CPC ......... *A61H 31/005* (2013.01); *A61B 5/0205* (2013.01); *A61B 5/026* (2013.01);
(Continued)

(58) Field of Classification Search
CPC .. A61H 31/005; A61H 9/0078; A61H 31/007; A61H 2201/1238; A61H 2201/5061; A61H 2201/5064; A61H 2201/5089; A61H 2201/5097; A61H 2205/084; A61H 2011/005; A61H 2031/001; A61H 2031/003;
(Continued)

(56) References Cited

U.S. PATENT DOCUMENTS 2,699,163 A  1/1955 Engstrom
2,899,955 A  8/1959 Huxley
(Continued)

FOREIGN PATENT DOCUMENTS

EP  2709581 B1  3/2014
KR  101383051 B1  4/2014
(Continued)

OTHER PUBLICATIONS

Plaisance et al., "Evaluation of an impedance threshold device in patients receiving active compression-decompression cardiopulmonary resuscitation for out of hospital cardiac arrest", Elsevier, Resuscitation 61 (2004) 265-271, www.elsevier.com/locate/resuscitation.
(Continued)

*Primary Examiner* — Quang D Thanh
(74) *Attorney, Agent, or Firm* — Nathaniel A. Wickliffe

(57) ABSTRACT

A system and method for mechanical CPR can include a device for providing compressive force to various locations on a patient, and biological monitoring systems to measure the effectiveness of the various locations of compressive force in pumping blood through the patient. The system can also include providing decompressive force to increase the efficacy of blood flow.

7 Claims, 14 Drawing Sheets

(51) Int. Cl.
*A61B 5/00* (2006.01)
*A61B 5/026* (2006.01)
*A61B 5/0205* (2006.01)
*A61B 5/113* (2006.01)

(52) U.S. Cl.
CPC ......... *A61B 5/4836* (2013.01); *A61H 9/0078* (2013.01); *A61H 31/007* (2013.01); *A61B 5/1135* (2013.01); *A61B 5/6823* (2013.01); *A61H 2201/1238* (2013.01); *A61H 2201/5061* (2013.01); *A61H 2201/5064* (2013.01); *A61H 2201/5089* (2013.01); *A61H 2201/5097* (2013.01); *A61H 2205/084* (2013.01)

(58) Field of Classification Search
CPC .... A61H 2201/1246; A61H 2201/1619; A61H 2201/1621; A61H 2201/5007; A61H 2201/5023; A61H 2201/5043; A61H 2201/5046; A61H 2203/0456; A61H 2230/00; A61H 2230/065; A61H 2230/085; A61H 2230/206; A61H 2230/208; A61H 2230/255; A61H 31/00; A61H 31/006; A61B 5/0205; A61B 5/026; A61B 5/4836; A61B 5/1135; A61B 5/6823; A61B 5/029; A61B 5/14542; A61B 5/361
See application file for complete search history.

(56) References Cited

U.S. PATENT DOCUMENTS

| | | | |
|---|---|---|---|
| 3,364,924 | A | 1/1968 | Barkalow |
| 3,481,327 | A | 12/1969 | Drennen |
| 3,683,655 | A | 8/1972 | White |
| 4,198,963 | A | 4/1980 | Barkalow |
| 4,349,015 | A | 9/1982 | Alferness |
| 4,397,306 | A | 8/1983 | Weisfeldt |
| 4,424,806 | A | 1/1984 | Newman |
| 4,664,098 | A | 5/1987 | Woudenberg |
| 4,770,164 | A | 9/1988 | Lach |
| 4,838,263 | A | 6/1989 | Warwick |
| 4,840,167 | A | 6/1989 | Olsson |
| 4,928,674 | A | 5/1990 | Halperin |
| 5,076,259 | A | 12/1991 | Hayek |
| 5,222,478 | A | 6/1993 | Scarberry |
| 5,454,779 | A | 10/1995 | Lurie |
| 5,490,820 | A | 2/1996 | Schock |
| 5,496,257 | A | 3/1996 | Kelly |
| 5,743,864 | A | 4/1998 | Baldwin, II |
| 5,769,800 | A | 6/1998 | Gelfand |
| 6,171,267 | B1 | 1/2001 | Baldwin, II |
| 6,174,295 | B1 | 1/2001 | Cantrell |
| 6,224,562 | B1 | 5/2001 | Lurie |
| 6,390,996 | B1 | 5/2002 | Halperin |
| 6,393,316 | B1 | 5/2002 | Gillberg |
| 6,418,342 | B1 | 7/2002 | Owen |
| 6,427,685 | B1 | 8/2002 | Ray, II |
| 6,752,771 | B2 | 6/2004 | Rothman |
| 6,827,695 | B2 | 12/2004 | Palazzolo |
| 6,869,409 | B2 | 3/2005 | Rothman |
| 7,032,596 | B2 | 4/2006 | Thompson |
| 7,220,235 | B2 | 5/2007 | Geheb |
| 8,795,208 | B2 | 8/2014 | Walker |
| 10,245,209 | B2 | 4/2019 | Lurie |
| 2001/0007928 | A1 | 7/2001 | Hansen |
| 2002/0026131 | A1 | 2/2002 | Halperin |
| 2003/0004445 | A1 | 1/2003 | Hall |
| 2004/0230140 | A1 | 11/2004 | Steen |
| 2006/0089574 | A1 | 4/2006 | Paradis |
| 2007/0010765 | A1 | 1/2007 | Rothman |
| 2007/0032829 | A1 | 2/2007 | Ostroff |
| 2007/0060785 | A1 | 3/2007 | Freeman |
| 2008/0097534 | A1 | 4/2008 | Myklebust |
| 2008/0275371 | A1 | 11/2008 | Hoffmann |
| 2012/0016179 | A1 | 1/2012 | Paradis |
| 2014/0155792 | A1 | 6/2014 | Karve |
| 2014/0213942 | A1 | 7/2014 | Hanson |
| 2014/0336546 | A1 | 11/2014 | Chapman |
| 2014/0358047 | A1 | 12/2014 | Lurie |
| 2015/0265497 | A1 | 9/2015 | Kaufman |
| 2016/0361228 | A1 | 12/2016 | Paradis |
| 2017/0035650 | A1* | 2/2017 | Taylor ..................... A61B 5/02 |
| 2017/0266078 | A1 | 9/2017 | Jayne |
| 2018/0021216 | A1 | 1/2018 | Paradis |
| 2018/0168922 | A1* | 6/2018 | Chapman ............. A61H 31/005 |
| 2019/0117501 | A1* | 4/2019 | Chapman ............. A61H 31/005 |

FOREIGN PATENT DOCUMENTS

| | | |
|---|---|---|
| KR | 20160146462 A | 12/2016 |
| WO | 2010099628 A1 | 9/2010 |
| WO | 2014051934 A1 | 4/2014 |
| WO | 2015048347 A1 | 4/2015 |

OTHER PUBLICATIONS

Liao et al., "Manual versus mechanical cardiopulmonary resuscitation. An experimental study in pigs", BMC Cardiovascular Disorders, Oct. 2010, 10:53, http://www.biomedcentral.com/1471-2261/10/53 (8 pages).

Lurie et a., "Improving active compression-decompression resuscitation with an inspiratory impedance valve", originally published Mar. 15, 1995, https://doi.org/10.1161/01.CIR.91.6.1629, Circulation. 1995; 91:1629-1632.

Lurie et al., "Improving standard cardiopulmonary resuscitation with an inspiratory impedance threshold valve in a porcine model of cardiac arrest", Anesth Analg 2001; 93:649-655.

Lafuente-Lafuente et al., "Active chest compression-decompression for cardiopulmonary resuscitation (Review)," The Cochrane Collaboration, 2009, Issue 3 (40 pages).

Bircher, N., et al, Do Intrathoracic Pressure Fluctuation or Heart Compressions Move Blood During External Cardiopulmonary Resuscitation (CPR)?, Resuscitation Research Center and the Department of Anesthesiology, University of Pittsburgh, ASA Abstract, V53, No. 3, Sep. 1980.

Cohen, Todd J., et al, Active Compression-Decompression, A New Method of Cardiopulmonary Resuscitation, JAMA, Jun. 3, 1992, vol. 267, No. 21, pp. 2916-2923.

Cohen, Todd J., et al, Active Compression-Decompression Resuscitation: A Novel Method of Cardiopulmonary Resuscitation, American Heart Journal, Nov. 1992, pp. 1145-1150.

Halperin, M.D., Henry R., A Preliminary Study of Cardiopulmonary Resuscitation by Circumferential Compression of the Chest with use of a Pneumatic Vest, The New England Journal of Medicine, vol. 329 No. 11, Sep. 9, 1993, pp. 162-768.

Kouwenhoven, W.B Closed-Chest Cardiac Massage, JAMA, Jul. 9, 1960, vol. 173, No. 10, pp. 1064-1067.

McDonald, M.D., John L, Systolic and Mean Arterial Pressures During Manual and Mechanical CPR in Humans, Annals of Emergency Medicine, 11:Jun. 6, 1982, pp. 292-295.

Ralston, Sandra H., Cardiopulmonary Resuscitation with Interposed Abdominal Compression in Dogs, Anesthesia and Analgesia, vol. 61, No. 8, Aug. 1982, pp. 645-651.

Voorhees, PhD, William D. et al, Improved Oxygen Delivery During Cardiopulmonary Resuscitation with Interposed Abdominal Compressions, Annals of Emergency Medicine, 12:Mar. 3, 1983, pp. 128-135.

Wolcke, Md., Benno G., et al, Comparison of Standard Cardiopulmonary Resuscitation Versus the Combination of Active Compression-Decompression Cardiopulmonary Resuscitation and an Inspiratory Impedance Threshold Device for Out-of-Hospital Cardiac Arrest, Circulation, 2003, pp. 108, 2201-2205.

Abella, Benjamin S. et al, CPR quality improvement during in-hospital cardiac arrest using a real-time audiovisual feedback system, Resuscitation, 2007, 73, pp. 54-61.

(56) References Cited

OTHER PUBLICATIONS

Babbs, MD, Charles F., Preclinical Studies of Abdominal Counterpulsation in CPR, Annals of Emergency Medicine, 13:Sep. 9, 1984, pp. 761-763.
Berkowitz, Ivor D., et al, Blood Flow during Cardiopulmonary Resuscitation with Simultaneous Compression and Ventilation in Infant Pigs, Pediatric Research, 1989, vol. 26, No. 6, pp. 558-564.
Paradis, Norman A., et al, Cardiac Arrest, The Science and Practice of Resuscitation Medicine, 2nd edition, Cambridge University Press 2007.
Haas, Thorsten, et al, Revisiting the cardiac versus thoracic pump mechanism during cardiopulmonary resuscitation, Resuscitation, 58, Nov. 5, 2002, pp. 113-116.
Jenkins, Constance, et al, Effects of the ResQPOD on Kinetics, Hemodynamics of Vasopressin, and Survivability in a Porcine Cardiac Arrest Model, Military Medicine, vol. 180, Sep. 2015, pp. 1011-1016.
Kleinman, Monica E., et al, Part 5: Adult Basic Life Support and Cardiopulmonary Resuscitation Quality: 2015 okmerican Heart Association Guidelines Update for Cardiopulmonary Resuscitation, and Emergency Cardiovascular Sare, Circulation, 2015, 132, S414-S435.
Michael, John R., et al, Mechanisms by with epinephrine augments cerebral and myocardial perfusion during ardiopulmonary resuscitation in dogs, Circulation 69, No. 4, 822-834, 1984.
Niemann Md., James T., Cough-CPR, Documentation of systemic perfusion in man and in an experimental model: a window to the mechanism of blood flow in external CPR, Critical Care Medicine, vol. 8, No. 3, pp. 141-146, Mar. 1980.
Paradis M.D., Norman A., Simultaneous Aortic, Jugular Bulb, and Right Atrial Pressures During Cardiopulmonary Resuscitation in Humans, Insights Into Mechanisms, Circulation, vol. 80, No. 2, Aug. 1989.
Plaisance, M.D., Patrick, A Comparison of Standard Cardiopulmonary Resuscitation and Active Compression-Decompression Resuscitation for Out-of-Hospital Cardiac Arrest, New England Journal of Medicine, vol. 341, No. 8, Aug. 19, 1999, pp. 569-575.
Segal, M.D., PhD, Nicolas, Intermittent Positive-Pressure Ventilation, Chest Compression Synchronized Ventilation, Bilevel Ventilation, Continuous Chest Compression, Active Compression Decompression, and Impedance Threshold Device—The Complexity of Ventilation During Cardiopulmonary Resuscitation, Critical Care Medicine, Feb. 2014, vol. 42, No. 2, pp. 480-481.
Wang, M.D., Chih-Hung, et al, Active Compression-Decompression Resuscitation and Impedance Threshold Device for Out-of-Hospital Cardiac Arrest: A Systematic Review and Metaanalysis of Randomized Controlled Trials, Critical Sare Medicine, Apr. 2015, vol. 43, No. 4, pp. 889-896.
Weisfeldt, M.D., M.L., et al, Increased intrathoracic pressure—no direct heart compression-causes the rise in intrathoracic vascular pressures during CPR in dogs and pigs, Critical Care Medicine, pp. 377-378, May 1981.
Yeung, J., et al, The use of CPR feedback/prompt devices during training and CPR performance: A systematic—eview, Resuscitation, 80, pp. 743-751, 2009.
Yang, Z., et al. A tourniquet assisted cardiopulmonary resuscitation augments myocardial perfusion in a porcine model of cardiac arrest, Resuscitation 86 (2015) 49-53.
Qvigstad et al., "Clinical pilot study of different hand positions during manual chest compressions monitored with capnography", Resuscitation 84 (2013) 1203-1207, www.elsevier.com/locate/resuscitation.
Aiello et al., "Real-time ventricular fibrillation amplitude-spectral area analysis to guide timing of shock delivery improves defibrillation efficacy during cardiopulmonary resuscitation in swine", Journal of the American Heart Association, DOI: 10.1161/JAHA.117.006749, pp. 1-15.

Aufderheide, T. P., et al. "Clinical evaluation of an inspiratory impedance threshold device during standard cardiopulmonary resuscitation in patients with out-of-hospital cardiac arrest." Crit Care Med. 33.4 (2005): 734-40.
Barkalow, B. H. "Comparison of miniaturized pneumatic chest compressor to Thumper." Resuscitation 79.3 (2008): 509.
Halperin, H. R., et al. "Cardiopulmonary resuscitation with a novel chest compression device in a porcine model of cardiac arrest: improved hemodynamics and mechanisms." J.Am.Coll.Cardiol. 44.11 (2004): 2214-20.
Ong, M. E., et al. "Use of an automated, load-distributing band chest compression device for out-of-hospital cardiac arrest resuscitation." JAMA 295.22 (2006): 2629-37.
Paradis, N. A. "Is this the next step for CPR?" Am. J. Emerg. Med. 18 34.1 (2016): 97-99.
Paradis, N. A., et al. "Coronary perfusion pressure during external chest compression in pseudo-EMD, comparison of systolic versus diastolic synchronization." Resuscitation 83.10 (2012): 1287-91.
Plaisance, P., et al. "Use of an inspiratory impedance threshold device on a facemask and endotracheal tube to reduce intrathoracic pressures during the decompression phase of active compression-decompression cardiopulmonary resuscitation." Crit Care Med. 33.5 (2005): 990-94.
Rudikoff, M. T., et al. "Mechanisms of Blood Flow During Cardiopulmonary Resuscitation." Circulation 61 (1980): 345-52.
Lurie, K.G., Improving active compression-decompression cardiopulmonary resuscitation with an inspiratory impedance value, ABSTRACT Circulation 1995; 91/6 (1 page abstract).
Sanders AB, Kern KB, Ewy GA, Atlas M, Bailey L. "Improved resuscitation from cardiac arrest with open-chest massage". Ann Emerg Med 1984; 13(9 Pt 1):672-675.
Stephenson HE, Corsan Reed L, Hinton JW. "Some Common Denominators in 1200 cases of cardiac arrest". Ann Surg 1953; 137:731-744.
Shinar Z, Bellezzo J, Paradis N et al. "Emergency department initiation of cardiopulmonary bypass: a case report and review of the literature". J Emerg Med 2012; 43(1):83-86.
Chan PS, McNally B, Tang F, Kellermann A. "Recent trends in survival from out-of-hospital cardiac arrest in the United States". Circ 2014; 130(21):1876-1882.
Cave DM, Gazmuri RJ, Otto CW et al. "Part 7: CPR techniques and devices: 2010 American Heart Association Guidelines for Cardiopulmonary Resuscitation and Emergency Cardiovascular Care". Circ 2010; 122(18 Suppl 3): S720-S728.
Hostler D, Everson-Stewart S, Rea TD et al. "Effect of real-time feedback during cardiopulmonary resuscitation outside hospital: prospective, cluster-randomised trial". BMJ 2011; 342:d512.
Stiell IG, Nichol G, Leroux BG et al. "Early versus later rhythm analysis in patients with out-of-hospital cardiac arrest". N Engl J Med 2011; 365(9):787-797.
Hallstrom A, Rea TD, Sayre MR et al. "Manual chest compression vs use of an automated chest compression device during resuscitation following out-of-hospital cardiac arrest: a randomized trial". JAMA 2006; 295(22):2620-2628.
Rubertsson S, Lindgren E, Smekal D et al. "Mechanical chest compressions and simultaneous defibrillation vs conventional cardiopulmonary resuscitation in out-of-hospital cardiac arrest: the LINC randomized trial". JAMA 2014 311(1):53-61.
Wik L, Olsen JA, Persse D et al. "Manual vs. integrated automatic load-distributing band CPR with equal survival after out of hospital cardiac arrest. The randomized CIRC trial". Resuscitation 2014; 85(6):741-748.
Esibov A, Banville I, Chapman FW, Boomars R, Box M, Rubertsson S. "Mechanical chest compressions improved aspects of CPR in the LINC trial". Resuscitation 2015; 91:116-121.
Plaisance P, Lurie KG, Payen D. "Inspiratory impedance during active compression-decompression cardiopulmonary resuscitation: a randomized evaluation in patients in cardiac arrest". Circ 2000; 101(9):989-994.
Neumann T, Gruenewald M, Lauenstein C, Drews T, Iden T, Meybohm P. "Hands-on defibrillation has the potential to improve the quality of cardiopulmonary resuscitation and is safe for rescuers—a preclinical study". J Am Heart Assoc 2012; 1(5):e001313.

(56) References Cited

OTHER PUBLICATIONS

Ong ME, Annathurai A, Shahidah A et al. "Cardiopulmonary resuscitation interruptions with use of a load-distributing band device during emergency department cardiac arrest". Ann Emerg Med 2010; 56(3):233-241.

Callaway, Clifton W.; Why We Should No. LongerTerminate Resuscitations after 20 Minutes; Mar. 2, 2016; Journal of Emergency Medical Services; vol. 41, Issue 3; (Year: 2016).

McClung, Christian D., et al.; Interposed Abdominal Compression CPR for an Out-of-Hospital Cardiac Arrest Victim Failing Traditional CPR; Oct. 20, 2015; Western Journal of Emergency Medicine; vol. XVI, No. 5; 690-692 (Year: 2015).

\* cited by examiner

METHODS AND DEVICES TO IMPROVE THE EFFICACY OF MECHANICAL CARDIOPULMONARY RESUSCITATION BY CHANGING THE POSITION OF CHEST COMPRESSION

RELATED APPLICATIONS

This application claims the benefit of U.S. Provisional Application Ser. No. 62/612,398, filed Dec. 30, 2017, entitled METHODS AND DEVICES TO IMPROVE THE EFFICACY OF MECHANICAL CARDIOPULMINARY RESUSCITATION BY CHANGING THE POSITION OF CHEST COMPRESSION, the entire disclosure of which is herein incorporated by reference.

FIELD OF THE INVENTION

This application relates to cardiopulmonary resuscitation (CPR), and more particularly, to mechanical systems and methods for providing efficacious CPR.

BACKGROUND OF THE INVENTION

Cardiopulmonary resuscitation (CPR) involves forces external to a patient that assist in pumping blood through the patient when the patient's own heart is not properly pumping blood by itself. CPR has been stuck at the manual chest compression stage for 50 years, generally requiring an individual providing CPR to kneel over the patient and press manually on the patient's chest repeatedly to pump blood.

Past innovations in CPR have included mechanical devices that replace manual human chest compressions with a mechanical piston that provide chest compressions, however, these devices are no more effective than manual CPR. Previously described mechanical and pneumatics systems for the provision of chest compression during CPR do not allow variations in the location of chest compression. All previous compression based devices and systems apply chest compression in a standard location, specifically the mid-sternum and in a vector that is vertical in both the sagittal and transverse planes. Previous systems also do not provide for active decompression in more than one location, but instead rely on only a single source of decompressive force in a single location. Recent studies have suggested that the most efficacious locations for chest compressions in CPR may not be the same for every person, and may not remain the same for a single person over time.

A personalized and customized approach is needed to improve CPR efficacy. More particularly, it is desirable to provide a personalized and customized approach to deliver the compressive force to a patient during CPR that has not been available using existing technology and devices.

SUMMARY OF THE INVENTION

This invention overcomes disadvantages of the prior art by providing a system and method providing compressive CPR force in varying locations, and for determining the most effective location for providing compressive force by monitoring feedback from one or more biological monitoring systems as compressive force is applied at varying locations, and using the feedback to compare the efficacy of different locations to determine the most effective location. The system and method can apply compressive force at the most effective location.

This invention can also overcome disadvantages of the prior art by providing compressive force to the patient along varying force vectors, and can vary the force vectors and determine the most effective force vector for providing compressive force by monitoring feedback from one or more biological monitoring systems as compressive force is applied at varying force vectors.

This invention can also overcome disadvantages of the prior art by providing active decompression in addition to compression during CPR compression cycles, and can vary the location and determine the most effective location for decompression and/or type of decompression by monitoring feedback from one or more biological monitoring systems as decompressive force is applied.

This invention can also overcome disadvantages of the prior art by providing compression and decompressive in multiple locations in sequence throughout each compression cycle to provide a pumping cycle, and can determine the most effective cycle of compression, decompression, and/or multiple compressions by using feedback from biological monitoring systems.

In an embodiment, a system for providing personalized CPR can include one or more pistons adapted to provide a compressive force at a plurality of locations on a patient, one or more biological monitoring systems adapted to measure feedback from one or more biological systems as the compressive force is applied at the plurality of locations on the patient, and a processor adapted to compare the feedback as compressive force is applied at a first location of the plurality of locations on the patient and at a second location of the plurality of locations on the patient. The system can include one or more pistons adapted to provide a decompressive force to the patient in sequence with the one or more pistons adapted to provide compressive force. The system can include one or more suction cups adapted to provide an active decompressive force to the patient. The system can include a mechanism to change one or more of the location, force, or vector of one or more of the pistons based on biologic feedback. The system can include a compression belt and a rotary compression unit. The system can include a rotary platform on the compression belt, wherein the rotary compression unit is mounted on the rotary platform. The system can include a backboard and a frame, wherein the one or more pistons are mounted to the frame. The one or more pistons can be pivotably mounted to the frame so that the force vector of the piston can be adjusted. The one or more pistons can include one or more upper pistons and one or more lower pistons, wherein the upper pistons are adapted to provide the compressive force to the patient, and the lower pistons are adapted to adjust the vector of the compressive force relative to the patient.

A system for providing personalized CPR can include one or more pistons operatively connected to suction cups adapted to provide a decompressive force at a plurality of locations on a patient, one or more biological monitoring systems adapted to measure feedback from one or more biological systems as the decompressive force is applied at the plurality of locations on the patient, and a processor adapted to compare the feedback as the decompressive force is applied at a first location of the plurality of locations on the patient and at a second location of the plurality of locations on the patient.

A method for providing personalized CPR can include applying a compressive force to a patient at a first location and releasing the compressive force at the first location in a first compression cycle, measuring biological feedback of the patient from a biological sensor during the first compression cycle at the first location, applying a compressive force to the patient at a second location and releasing the compressive force at the second location in a second compression cycle, measuring biological feedback of the patient from the biological sensor during the second compression cycle at the second location, and comparing the biological feedback of the patient measured during the first compression cycle to the biological feedback of the patient measured during the second compression cycle to determine a best location for a best compression cycle that provides the best blood flow for the patient. The method can include applying a compressive force to the patient at a new location and releasing the compressive force at the new location in a new compression cycle, measuring biological feedback of the patient from the biological sensor during the new compression cycle at the new location, and comparing the biological feedback of the patient measured during the new compression cycle to the biological feedback of the patient measured during the best compression cycle to determine a new best location for a new best compression cycle. The method can include applying a decompressive force to a patient at a first decompression location and releasing the decompressive force at the first decompression location in a first decompression cycle, measuring biological feedback of the patient from the biological sensor during the first decompression cycle, applying a decompressive force to the patient at a second location and releasing the decompressive force at the second location in a second decompression cycle, measuring biological feedback of the patient from the biological sensor during the second decompression cycle, and comparing the biological feedback of the patient measured during the first decompression cycle to the biological feedback of the patient measured during the second decompression cycle to determine a best location for a best decompression cycle that provides the best blood flow for the patient. Applying a decompressive force can include providing active suction.

BRIEF DESCRIPTION OF THE DRAWINGS

The invention description below refers to the accompanying drawings, of which.

DETAILED DESCRIPTION

Figure 1:
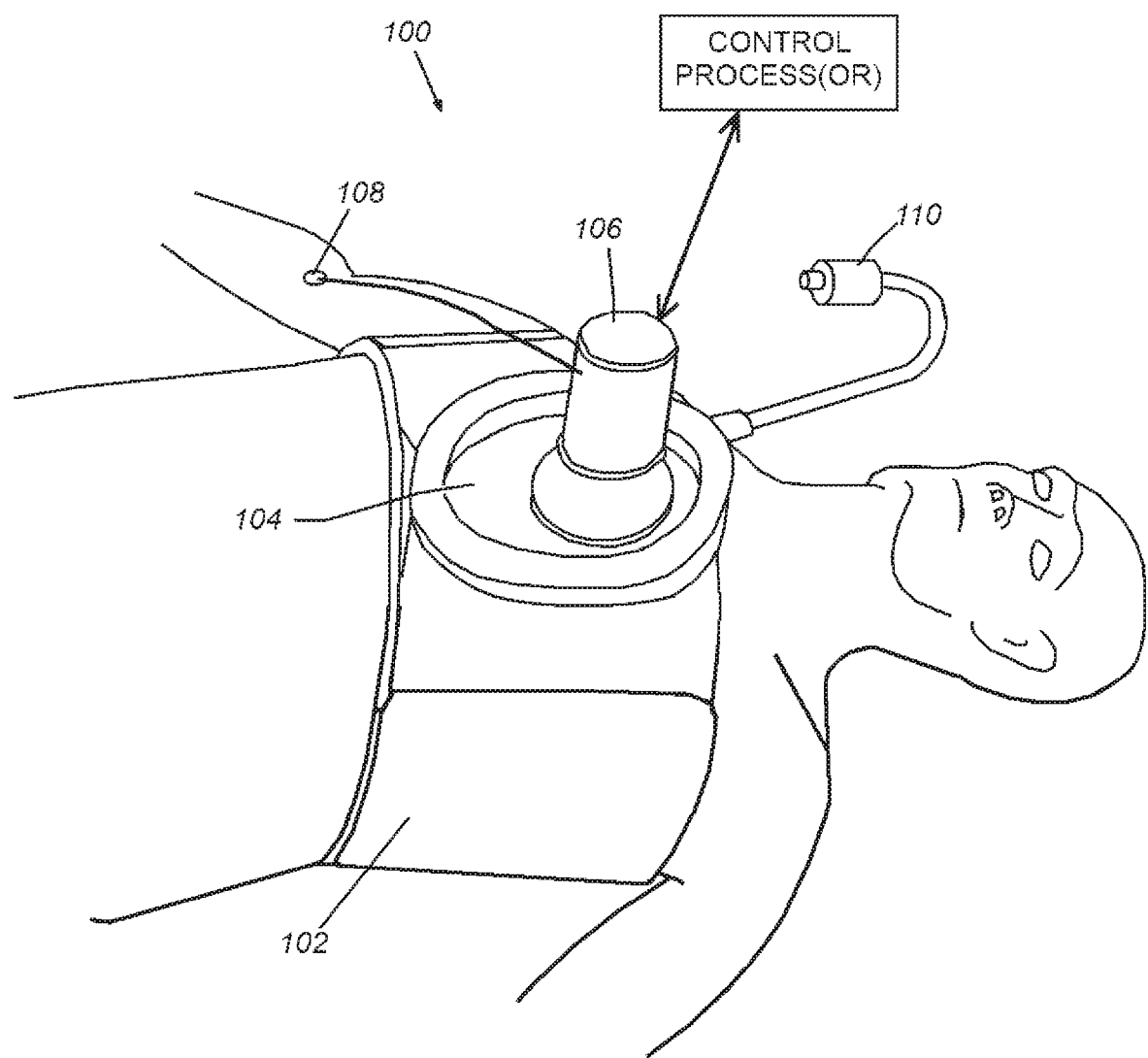
FIG. 1 is a perspective view of a mechanical CPR system with a compression belt and mobile compression unit according to an illustrative embodiment.

The hemodynamic efficacy of cardiopulmonary resuscitation (CPR) in pumping blood may be improved by applying compression in different locations on the chest. Depending on the patient's individual anatomy, compression of the chest in the standard location, at or slightly above or below the mid-sternum, may be sub-optimal for pumping blood. This location may not optimally compress the cardiac pump mechanism and/or interfere/obstruct the ventricular outflow tracts. Not only might the standard location be suboptimal, but the standard vertical axis may not be the optimal vector. Furthermore, chest deformity or loss of elastic recoil may develop as CPR chest compressions are applied, and the optimal location may change over time.

Standard mechanical systems for the provision of CPR chest compressions are limited to single-piston single-location mechanisms. The present disclosure provides that a piston with a movable position or multiple pistons can allow compression of the chest in one or more non-standard locations so as to achieve improved efficacy. The location of compression can be varied, and validated biomarkers can be used to determine which locations are most effective. The most effective location can change over time, and the system and method described herein can repeatedly check for better locations. The present disclosure also provides that a piston with a movable location or multiple pistons can allow active decompression of the chest in one or more locations so as to achieve improved efficacy. Active decompression can include pulling up and/or out on the chest as part of a pumping cycle to improve blood flow. The present invention can include mechanical and/or pneumatics systems for the provision of chest compression during CPR, and can include compression of the chest by one or more pistons in varying locations along with active decompression of the chest by one or more pistons that can include suction-pistons, and can be in locations that can be different from the compression locations and/or locations that are the same as the compression locations. Active decompression can provide a synergistic effect in combination with compression that can result in efficacy of the CPR system that is greater than the sum of the efficacy of compression used alone and the efficacy of decompression used alone.

The present invention can vary the location of compression on the chest along with varying patterns of chest compression or constriction based on feedback from indicators of hemodynamics, organ or tissue status, or patient status. The present invention can include a multiple piston array design, and can include variation in the angular vector of one or more pistons. The present invention can also include varying locations of constriction to one or more parts of the body using one or more constriction belts, pneumatic bladders, hydraulic bladders, or other systems. Constriction and/or compression can be applied to one or more of various compartments in the body. Constriction and/or compression can be applied to the thorax, abdomen, heart, and/or limbs individually or in combination to increase blood flow.

A mechanical system for the provision of chest compression during CPR can allow variation in the location of chest compression and/or decompression, and can allow manual, automatic, or mechanical variation in the position of chest compression and/or decompression during CPR. In various embodiments, there can be a single-piston mechanism, and its location can be varied by alteration of a piston supporting gantry. The piston mechanism can be powered in any standard manner including pneumatic or mechanical means. In various embodiments, the system and method can incorporate multiple pistons arrayed in a manner so as to allow compression and/or decompression of the chest in a number of different locations without adjustment of the supporting structures. The pistons can be incorporated into a multi-piston mechanism and/or structure positioned anterior to the patient's chest. In various embodiments of the system and method, the multi-piston platform can have a central piston positioned in the standard manner over the mid-sternum at or just below the male inter-nipple line. Additional pistons can be incorporated radially around the central piston. In various embodiments, individual piston(s) may be adjustable in orientation angle to the patient in both the cephalad-caudad and medial-lateral planes.

The system and method can include one or more hydraulic and/or pneumatic bladders that can apply compression to the patient at one or more locations. A multi-piston or multi-bladder array can allow sequential patterns of varying force and depth. In various embodiments, the pattern of pneumatic filling may be varied so as to achieve various patterns or locations of chest constriction.

Individual pistons that can include suction-cup capability can also provide active decompression of the chest, which can be adjustable as to location, vector, and/or force. Active decompression may be achieved by multiple pistons simultaneously or in sequence. The pattern of multi-piston active decompression may be variable and adjustable.

Mechanical or pneumatic activation of a specific piston can allow chest compressions and/or decompressions in differing locations left or right laterally and/or cephalic or caudal to the central piston location. Chest compression and/or decompression can be achieved by multiple pistons simultaneously or in sequence. Activation of multiple pistons in varying patterns can achieve a summary compression of the chest. Activation of multiple pistons in varying amounts of force can achieve a summary active decompression of the chest. The system and method can allow modification of each individual piston's specific depth of compression. The system and method can allow modification of individual piston's force vectors. The system and method can allow activation of multiple pistons in sequence such that the force, depth, and/or decompression patterns can be varied to create a pattern that enhances cardiac output. The system and method can allow activation of multiple pistons in sequence such that the force, depth, and/or decompression patters can be varied to create a pattern that enhances venous return.

The system and method can allow active compression of the chest in one location and decompression in another location or the same location, along with a mechanism to vary these locations over time. Variations can be based on biofeedback. Various modification can be controlled manually by the operator or can be controlled by algorithms of the system. Modifications can be controlled based on a play-the-winner system with various modifications compared against one another. The system and method described herein can apply compressive force to multiple locations, and can apply decompression to multiple locations to determine the best locations for compression and decompression in a compression cycle. The system and method can determine that the best location(s) and/or vector(s) have changed over time and can change the location(s) and/or vector(s).

The use of multiple pistons and piston positions with adjustable mechanisms can be combined to achieve simultaneous circumferential constriction of the chest. Varying pistons can be combined with a circumferential constriction mechanism. Pneumatic bladders can be used in combination with or in place of pistons. Position adjustability can be used in abdominal counterpulsation during CPR. Individual piston's specific force vectors can be modified. Individual piston's specific depth of compression can be modified.

In an embodiment, the actuator(s) of the multi-piston head can be under operator control and the powering of any specific piston can be selected by the clinician. In various embodiments, the actuator or controller of a multi-piston head can be under automated microprocessor control based on feedback from biological measurements of the patient's status such as cardiac output, tissue oxygen status, ET-CO2, and/or variants of median ventricular frequency. The controlling algorithm may select the optimal piston or pistons based on a "play the winner" measurement of efficacy. By way of non-limiting example, this can mean that the after a predetermined length of time, such as 30 seconds or a minute, the system can switch to a different compression location for a predetermined length of time, such as 30 seconds, and can determine based on feedback measurements whether the new compression location results in improved or decreased efficacy, and the most efficacious compression location can be the winner (i.e. the best location). After the winner is used for a predetermined length of time, such as 30 seconds or a minute, the system can switch to a different compression location for a predetermined length of time, such as 30 seconds, and can continue to iteratively repeat the "play the winner" system based on feedback measurements.

FIG. 1 is a perspective view of a mechanical CPR system with a compression belt and mobile compression unit, according to an illustrative embodiment. The mechanical CPR system 100 can include a compression belt 102, a rotary platform 104, and a compression unit 106 on the rotary platform 104. The compression unit can be positioned off-center on the rotary platform, and the rotary platform 104 can rotate within the compression belt 102 to adjust the location of the compression unit 106. Rotation of the rotary platform can be accomplished though mechanical means that should be clear to one skilled in the art, such as, by way of non-limiting example, the rotary platform 104 can have teeth around the circumference of the rotary platform 104, and the rotary platform 104 can be rotated by a motor in the compression belt 102 that can engage with the teeth of the rotary platform 104.

The compression unit 106 can include one or more pistons within the compression unit. The one or more pistons can be positioned off-center within the compression unit 106, and the compression unit 106 can rotate relative to the rotary platform 104 to adjust the location of the one or more pistons relative to the patient. Rotation of the compression unit can be accomplished though mechanical means that should be clear to one skilled in the art.

The mechanical CPR system can include one or more sensors 108 that can monitor the biological systems of the patient. The one or more sensors can include a cardiac output sensor, a tissue oxygen sensor, an ET-CO2 sensor, a venous flow sensor, a ventricular fibrillation frequency sensor, and/or a pulse sensor.

The mechanical CPR system can include one or more control processors that can be located within the compression belt or the compression unit. The mechanical CPR system can include a connector 110 that can connect the mechanical CPR system to various external devices that can include one or more processors, hydraulic and/or pneumatic compressors, electrical inputs, biological monitoring system(s), and/or other external systems.

In various embodiments, compression belt 102 can provide compression to the torso, and can include one or more pneumatic or hydraulic bladders that can provide compression to the torso. In various embodiments, compression belt 102 can provide circumferential constriction around a portion of the torso of the patient.

Figure 2:
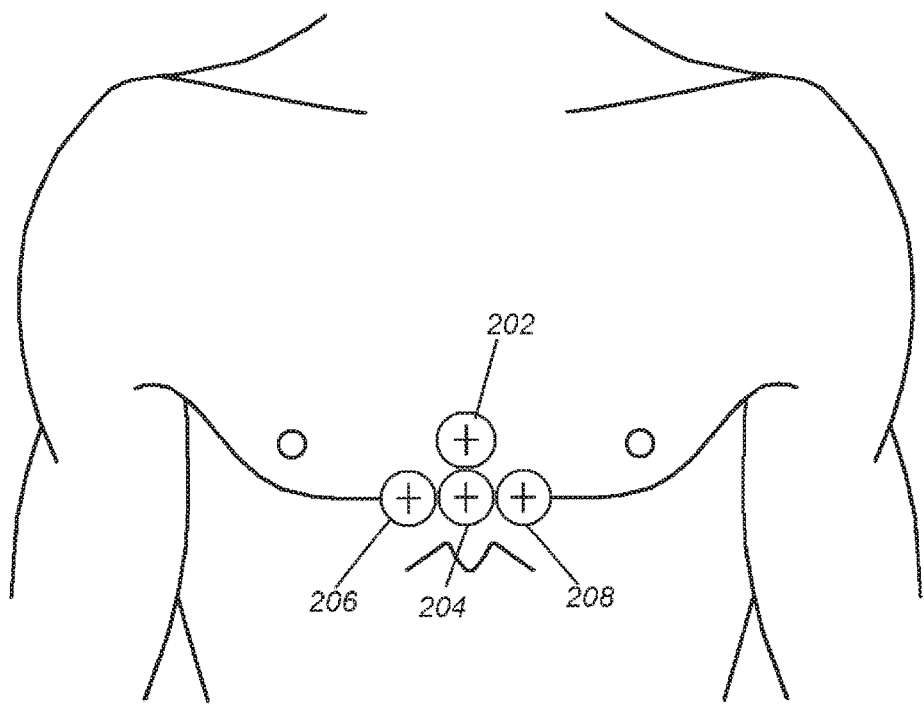
FIG. 2 is a diagrammatic view of a human torso with exemplary locations for contact during mechanical CPR, according to an illustrative embodiment.

FIG. 2 is a diagrammatic view of a human torso with exemplary locations for contact during mechanical CPR, according to an illustrative embodiment. Location 202 has been the standard position for chest compressions in CPR. However, studies have shown that for many patients, locations 204, 206, and/or 208 may be more efficacious locations for compression than location 202. In many patients, combinations of locations or changing locations can be most efficacious.

Figure 3:
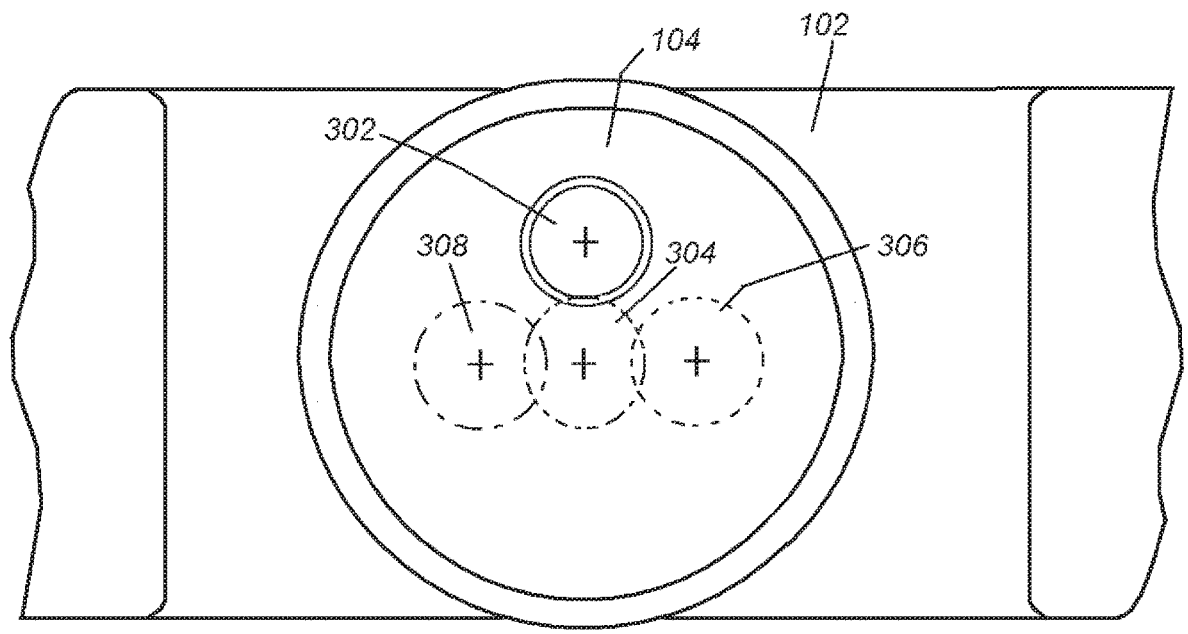
FIG. 3 is a diagrammatic view of the inside of a mechanical CPR system with a compression belt, showing exemplary locations of contact during mechanical CPR, according to an illustrative embodiment.

FIG. 3 is a diagrammatic view of the inside of a mechanical CPR system with a compression belt, showing exemplary locations of contact during mechanical CPR, according to an illustrative embodiment. The use of a rotary platform 104 and/or rotation of the compression unit 106 can allow the position(s) of the one or more pistons to be adjusted to an infinite number of positions that can include positions 302, 304, 306, and 308 that can correspond to locations 202, 204, 206, and 208. The system and method described herein allows chest compressions and/or decompression to be applied to various locations on the patient's torso. Biological feedback can be used to determine the most efficacious position(s) for the piston(s), and piston positions can be varied throughout the CPR procedure.

Figure 4:
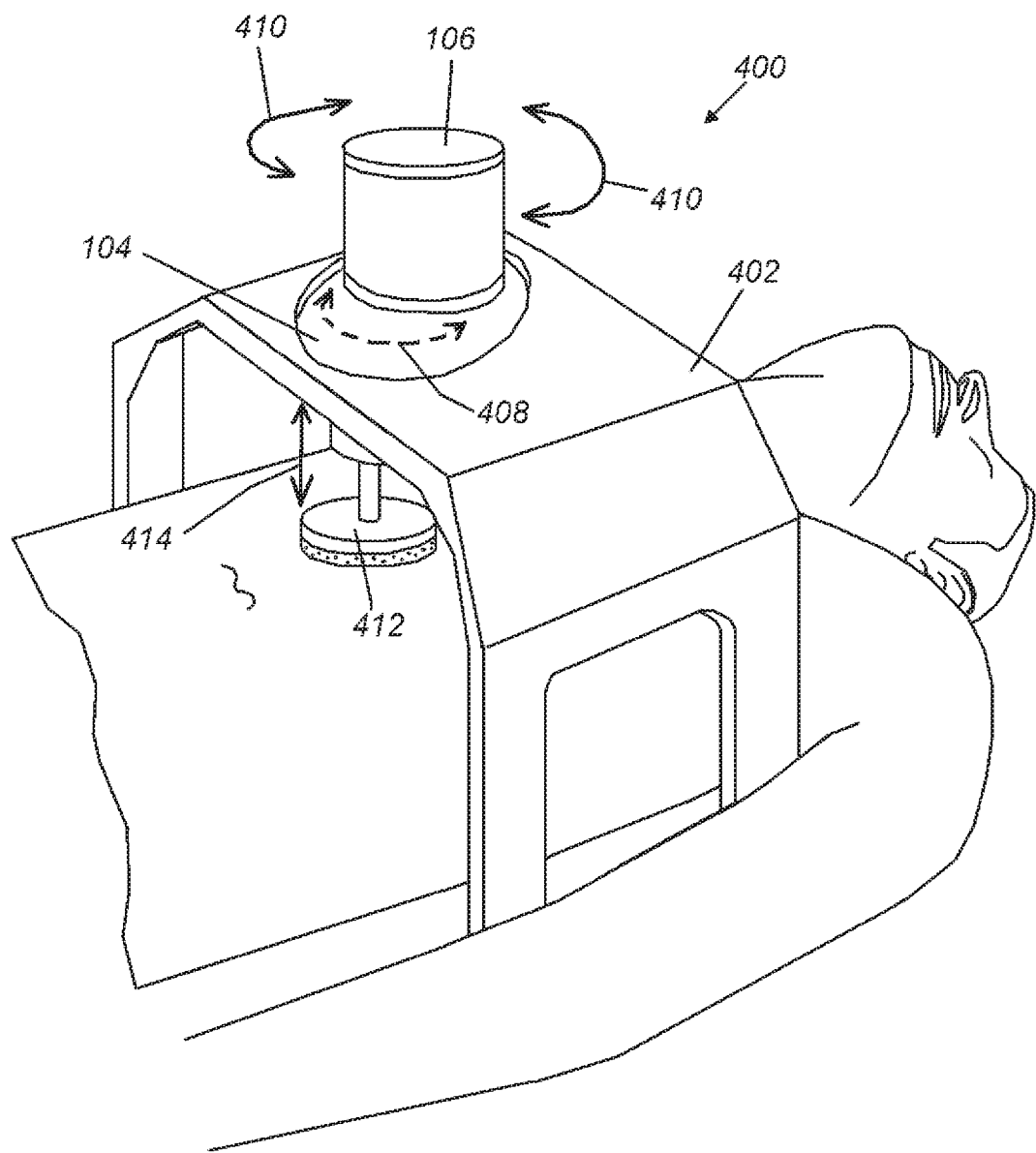
FIG. 4 is a perspective view of a mechanical CPR provider with a frame and a mobile compression unit, according to an illustrative embodiment.

FIG. 4 is a perspective view of a mechanical CPR provider with a frame and a mobile compression unit, according to an illustrative embodiment. A mechanical CPR provider 400 can include a frame 402 that can be used in conjunction with a backboard (not shown). Frame 402 can include a rotary platform 104, and a compression unit 106 on the rotary platform 104. The rotary platform 104 can rotate within the frame 402 along arrow 408 to adjust the position of the compression unit 106. The compression unit 106 can include one or more pistons within the compression unit. The compression unit 106 can rotate relative to the rotary platform 104 along arrows 410 to adjust the location of the one or more pistons. The mechanical CPR provider 400 can include one or more CPR heads 412 that can be operatively connected to the one or more pistons of the compression unit 106. CPR heads 412 can move along arrows 414 and can make contact with and compress the patient's torso at various locations. The use of a rotary platform 104 and/or rotation of the compression unit 106 can allow the position(s) of the one or more CPR heads to be adjusted to an infinite number of positions. The mechanical CPR system can include one or more control processors that can be located within the frame or the compression unit.

Figure 5:
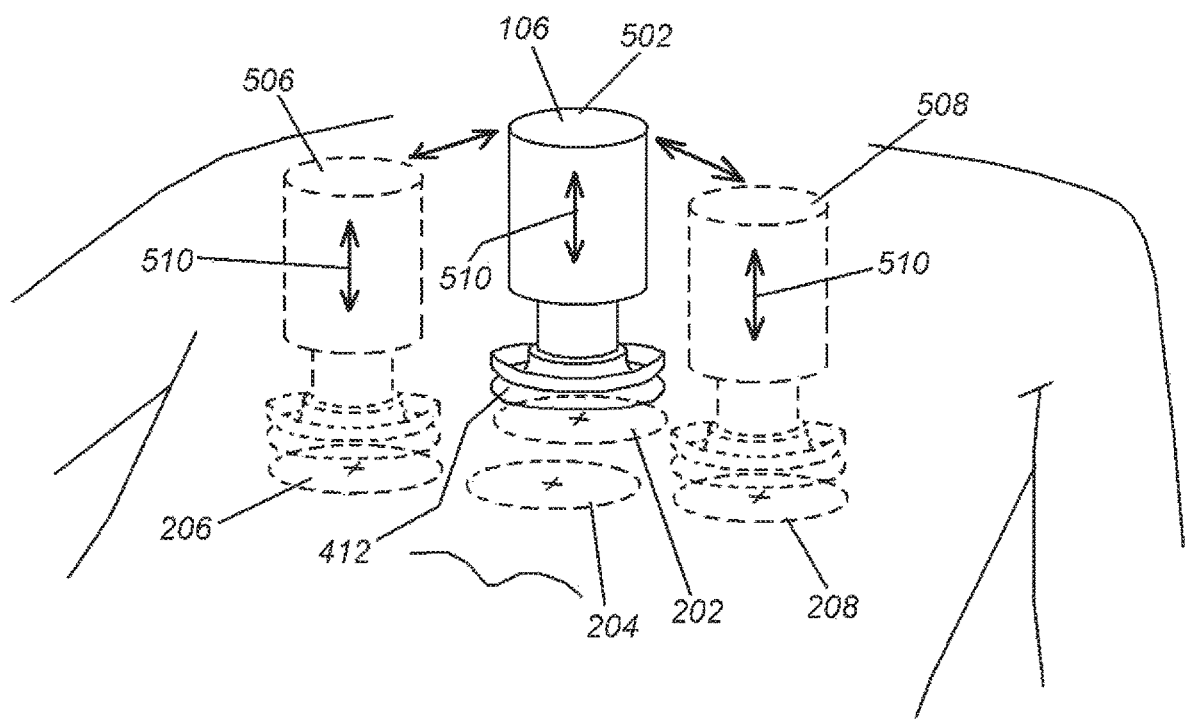
FIG. 5 is a perspective view of various positions for the mobile compression unit over different locations for contact during mechanical CPR, according to an illustrative embodiment.

FIG. 5 is a perspective view of various positions for the mobile compression unit over different locations for contact during mechanical CPR, according to an illustrative embodiment. The mobile compression unit 106 can be moved between positions 502, 506, 508, and other positions, to locate the CPR head 412 over locations 202, 204, 206, 208, and other locations. The mobile compression unit 106 can include one or more pistons that can extend the CPR head against the torso along arrows 510 to provide compression, and can retract the CPR head 412 along arrows 510 after compression.

Figure 6A:
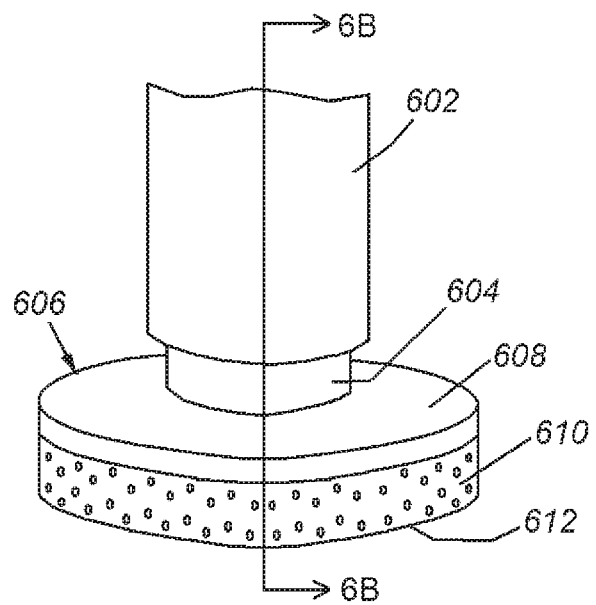
FIG. 6A is a perspective view of a mechanical CPR head, according to an illustrative embodiment.
Figure 6B:
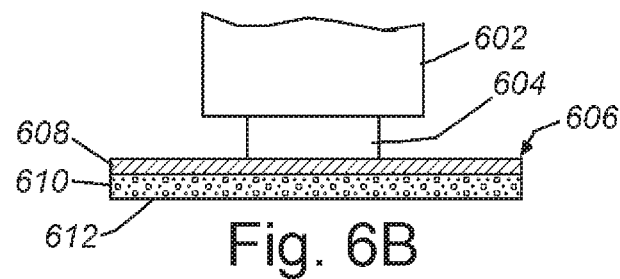
FIG. 6B is a cross section of the mechanical CPR head of FIG. 6A, taken through line 6B-6B of FIG. 6A, according to the illustrative embodiment.

FIG. 6A is a perspective view of a mechanical CPR head, according to an illustrative embodiment, and FIG. 6B is a cross section of the mechanical CPR head of FIG. 6A, taken through line 6B-6B of FIG. 6A, according to the illustrative embodiment. An actuator 602 can move a piston 604 that can be connected to the CPR head 606. In various embodiments the CPR head 606 can be a single component or can include multiple components. The mechanical CPR head 606 can include a rigid or semi-rigid support 608 and a soft or semi-soft pad 610. In various embodiments, a CPR head can include an adhesive 612 on the bottom of the pad 610 that can adhere the CPR head to the patient to provide active decompression.

Figure 7A:
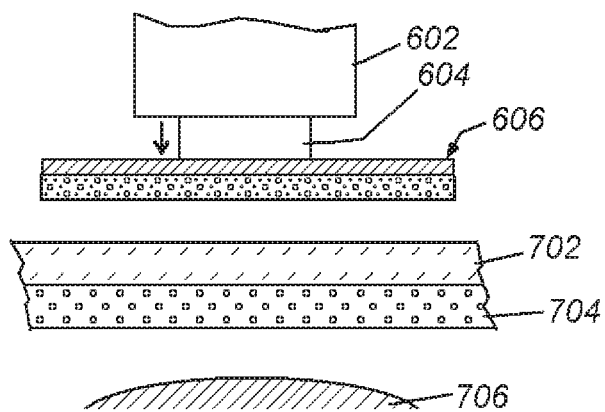
FIG. 7A is the cross section of the mechanical CPR head of FIG. 6B, shown prior to administering compression to a torso of a patient, according to an illustrative embodiment.
Figure 7B:
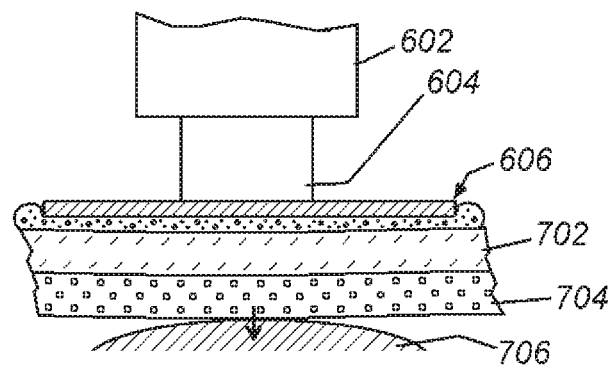
FIG. 7B is the cross section of the mechanical CPR head of FIG. 6B, shown after administering compression to a torso of a patient, according to an illustrative embodiment.

FIG. 7A is the cross section of the mechanical CPR head of FIG. 6B, shown prior to administering compression to a torso of a patient, according to an illustrative embodiment. The torso of the patient can include skin 702, sternum 704, and the heart 706. The actuator 602 can move the piston 604 to drive the CPR head 606 along arrow 710 to make contact with the patient. FIG. 7B is the cross section of the mechanical CPR head of FIG. 6B, shown after administering compression to a torso of a patient, according to an illustrative embodiment. The actuator 602 can move the piston 604 to drive the CPR head 606 to provide compression to the heart 706.

Figure 8A:
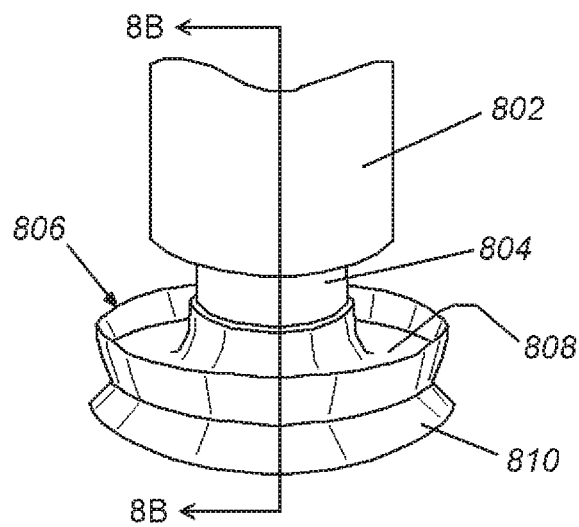
FIG. 8A is a perspective view of a mechanical CPR head with a suction cup, according to an illustrative embodiment.
Figure 8B:
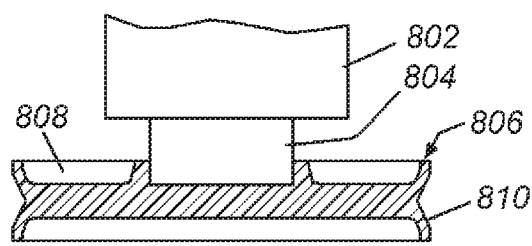
FIG. 8B is a cross section of the mechanical CPR head with a suction cup of FIG. 8A, taken through line 8B-8B of FIG. 8A, according to the illustrative embodiment.

FIG. 8A is a perspective view of a mechanical CPR head with a suction cup, according to an illustrative embodiment, and FIG. 8B is a cross section of the mechanical CPR head with a suction cup of FIG. 8A, taken through line 8B-8B of FIG. 8A, according to the illustrative embodiment. An actuator 602 can move a piston 604 that can be connected to the CPR head 806. In various embodiments the CPR head 806 can be a single component or can include multiple components. The mechanical CPR head 806 can include a rigid or semi-rigid support 808 and a suction cup 810. Suction cup 810 can be passive, or can be connected to a suction source that can provide a vacuum to help secure the suction cup 810 to the patient to provide active decompression.

Figure 9A:
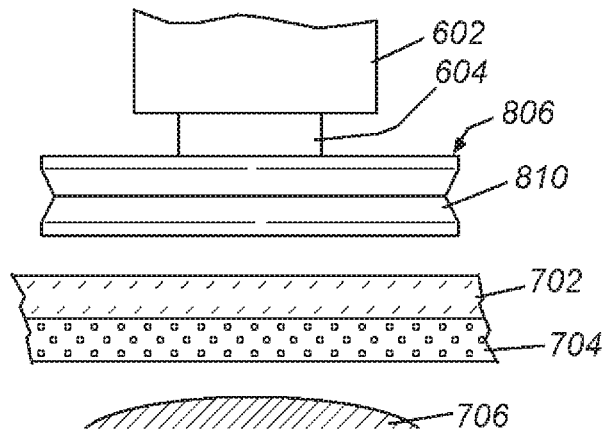
FIG. 9A is the cross section of the mechanical CPR head with a suction cup of FIG. 8B, shown prior to administering compression to a torso of a patient, according to an illustrative embodiment.
Figure 9B:
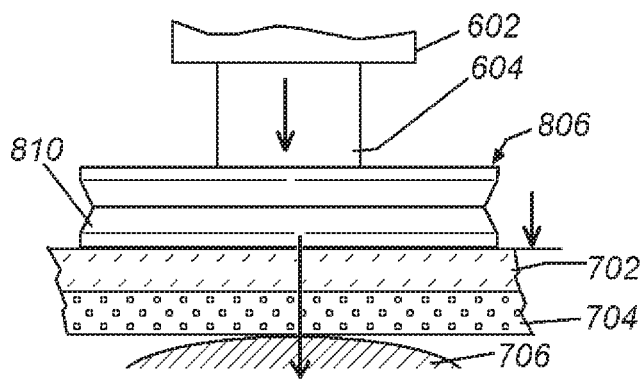
FIG. 9B is the cross section of the mechanical CPR head of FIG. 8B, shown after administering compression to a torso of a patient, according to an illustrative embodiment.
Figure 9C:
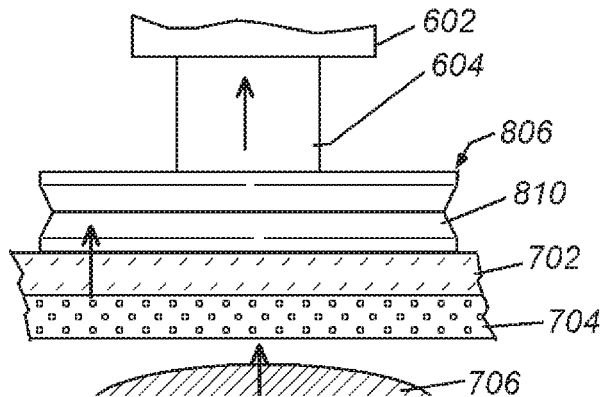
FIG. 9C is the cross section of the mechanical CPR head of FIG. 8B, shown administering decompression to a torso of a patient, according to an illustrative embodiment.

FIG. 9A is the cross section of the mechanical CPR head with a suction cup of FIG. 8B, shown prior to administering compression to a torso of a patient, according to an illustrative embodiment. The actuator 602 can move the piston 604 to drive the CPR head 806 with suction cup 810 to make contact with the patient. FIG. 9B is the cross section of the mechanical CPR head of FIG. 8B, shown after administering compression to a torso of a patient, according to an illustrative embodiment. The actuator 602 can move the piston 604 to drive the CPR head 806 with suction cup 810 to provide compression to the heart 706. FIG. 9C is the cross section of the mechanical CPR head of FIG. 8B, shown administering decompression to a torso of a patient, according to an illustrative embodiment. After compression has been applied, the actuator 602 can pull up on the piston 604 and CPR head 806 with the suction cup 810 to pull on the torso of the patient and provide decompression. In various embodiments, the compression and decompression can include an approximately two inch stroke distance.

Figure 10:
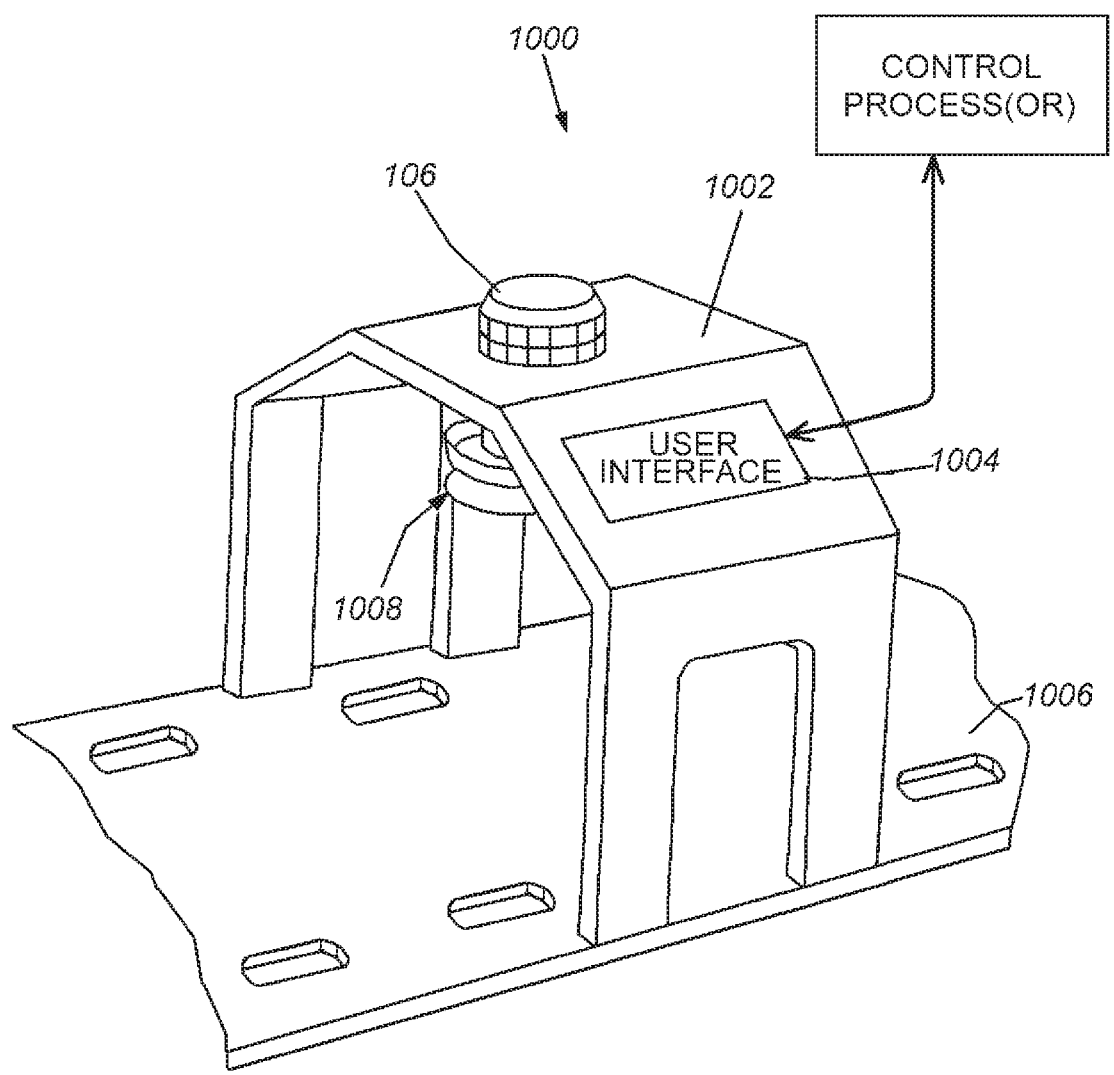
FIG. 10 is a perspective view of a mechanical CPR provider with a frame supporting one or more actuators, according to an illustrative embodiment.

FIG. 10 is a perspective view of a mechanical CPR provider with a frame supporting one or more actuators, according to an illustrative embodiment. The mechanical CPR provider 1000 can include a user interface 1004 on the frame 1002. The interface can be part of any acceptable computing device with a display and/or touchscreen. In embodiments, the interface 1004 can be all, or partially, implemented as a remote device, such as a laptop or smartphone that is interconnected with the circuitry of the frame by a wired and/or wireless link (e.g. 802.11/WiFi, Bluetooth®, etc.). Some or all of the control functions of the device can be carried out by a processor associated with the interface 1004. The mechanical CPR provider 1000 can include a backboard 1006 that can be positioned under the patient, and the frame 1002 can be secured to the backboard 1006. The mechanical CPR provider 1000 can have one or more actuators that can be operatively connected to one or more CPR heads 1008. In various embodiments, the actuators can be part of a compression unit 106 that can be a rotatable compression unit or can be a compression unit that remains in a fixed position. In various embodiments, a mechanical CPR provider can be free of a rotary platform. In various embodiments, a mechanical CPR provider can have a plurality of actuators mounted to the frame 1002 in fixed positions.

Figure 11:
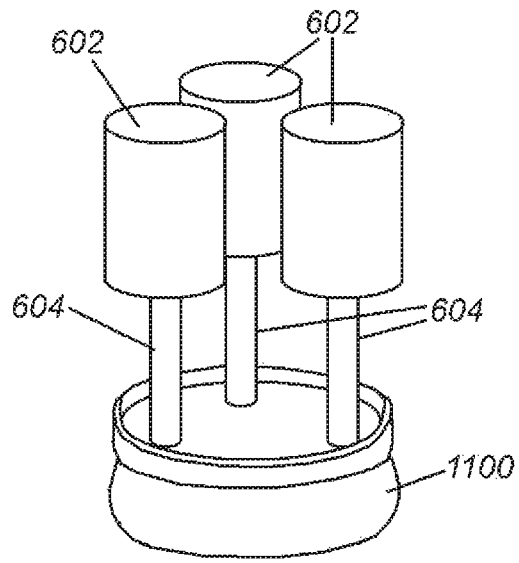
FIG. 11 is a perspective view of a mechanical CPR head with multiple actuators, according to an illustrative embodiment.

FIG. 11 is a perspective view of a mechanical CPR head with multiple actuators, according to an illustrative embodiment. A plurality of actuators 602 with pistons 604 can be connected to a single CPR head 1100. The actuators 602 can be part of a compression unit that can be mobile, or the actuators 602 can be mounted directly to a frame. Each actuator 602 can be controlled separately, so that the location of the force and the vector of the force applied to the torso of the patient can be adjustable. The location of the force and/or the vector of the force can be adjusted throughout the CPR process, and the adjustments can be based on feedback from one or more biological monitoring systems.

Figure 12:
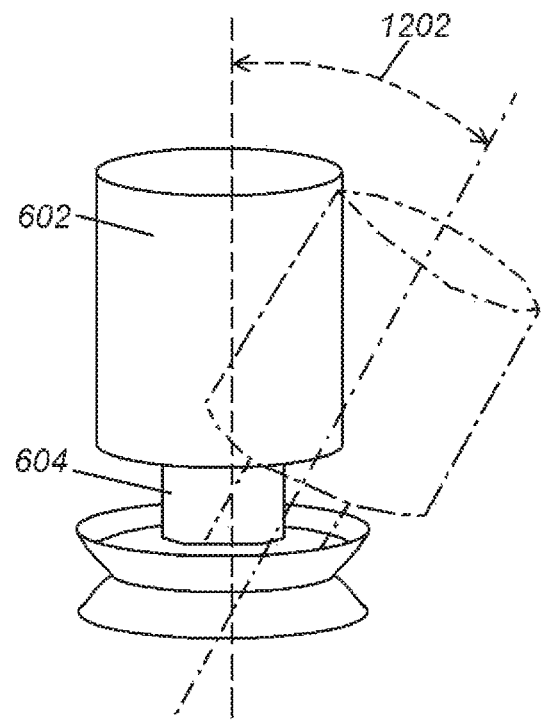
FIG. 12 is a perspective view of a mechanical CPR actuator with an adjustable angle, according to an illustrative embodiment.

FIG. 12 is a perspective view of a mechanical CPR actuator with an adjustable angle, according to an illustrative embodiment. The actuator 602 can be adjustably mounted to the mechanical CPR provider. The angle of the piston 604 can be varied along arrow 1202 to change the location of the force of the CPR head against the patient to provide compression in a variety of locations. The angle of the piston 604 can be varied along arrow 1202 to change the direction of the force vector of the CPR head against the patient to provide compression along a range of force vectors. The angle of the piston 604 can be varied along arrow 1202 to change the location of the force of the CPR head to provide decompression in a variety of locations. The angle of the piston 604 can be varied along arrow 1202 to change the direction of the force vector of the CPR head to provide decompression along a range of force vectors.

Figure 13A:
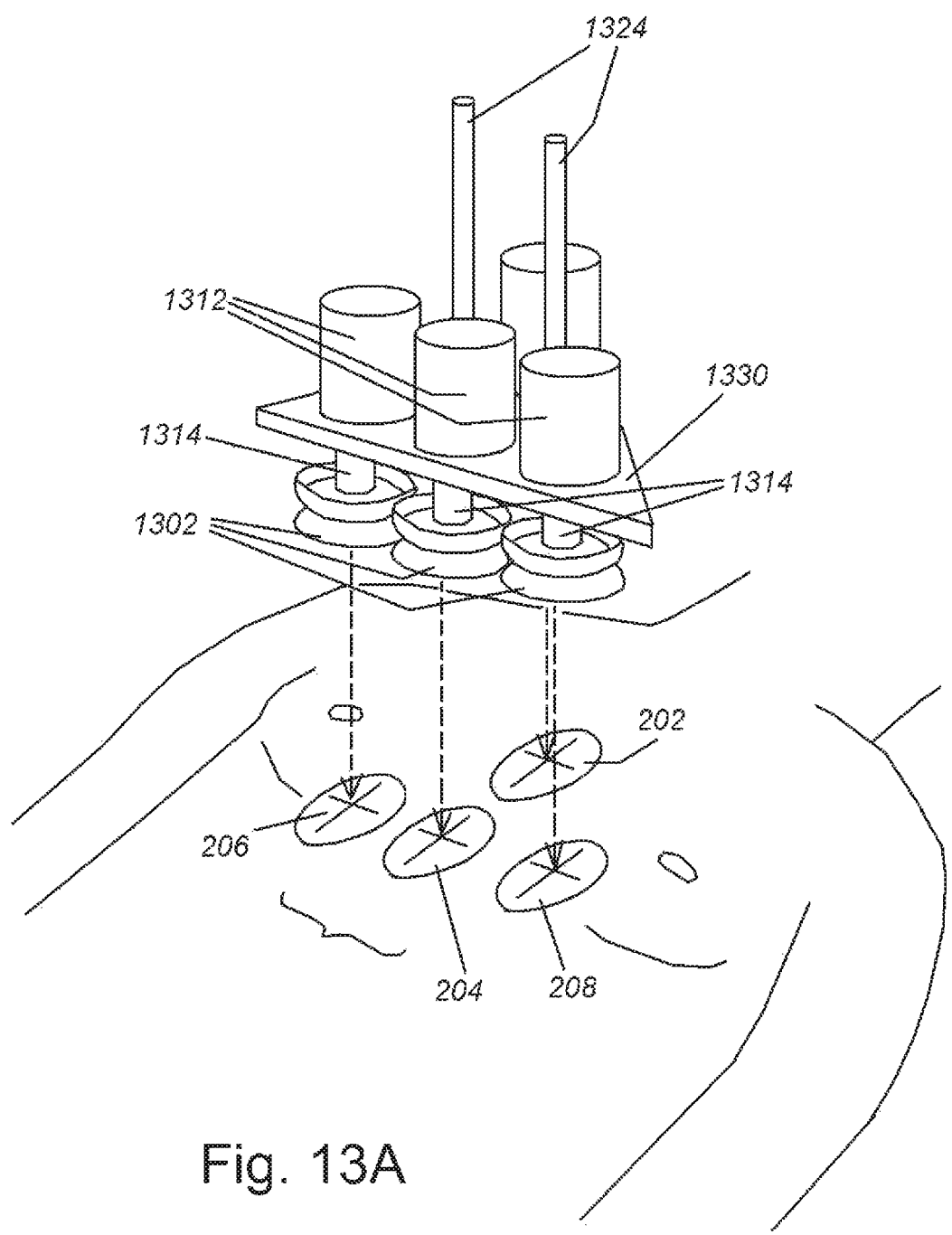
FIG. 13A is a perspective view of a mechanical CPR system with multiple actuators, according to an illustrative embodiment.

FIG. 13A is a perspective view of a mechanical CPR system with multiple actuators, according to an illustrative embodiment. The mechanical CPR system can have multiple CPR heads 1302 that can be aligned with multiple locations on the patient that can include locations 202, 204, 206, and/or 208. The mechanical CPR system can have multiple lower actuators 1312 and lower pistons 1314. Each CPR head 1302 can be operatively connected to one or more lower pistons 1314, and the lower pistons 1314 can be driven by lower actuators 1312. In various embodiments, lower actuators 1312 can be adjustably mounted so that the vector of force can be adjusted.

Figure 13B:
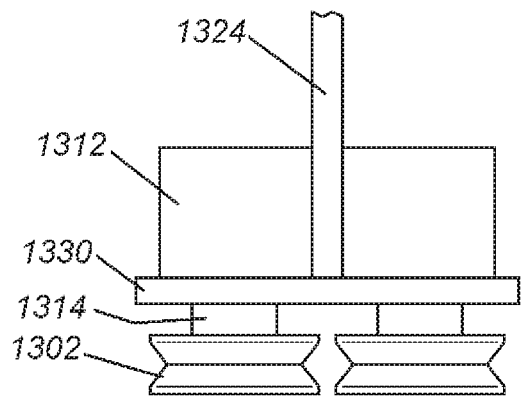
FIG. 13B is a side view of the mechanical CPR system with multiple actuators of FIG. 13A, according to the illustrative embodiment.

In various embodiments, the mechanical CPR system can have lower actuators 1312 and lower pistons 1314, and can have one or more upper actuator(s) (not shown) and one or more upper piston(s) 1324. In embodiments with upper and lower pistons, the upper piston(s) 1324 can be operatively connected to a mounting plate 1330, and the lower actuators 1312 can be operatively connected to the mounting plate 1330. This system can allow combinations of pistons to be actuated so that force can be applied to the patient in various locations and at various vectors. FIG. 13B is a side view of the mechanical CPR system with multiple actuators of FIG. 13A, according to the illustrative embodiment. The system can have multiple lower actuators 1312 and lower pistons 1314 that can be operatively connected to CPR heads 1302. The system can have a mounting plate 1330 and upper pistons 1323 operatively connected to the mounting plate.

Figure 14A:
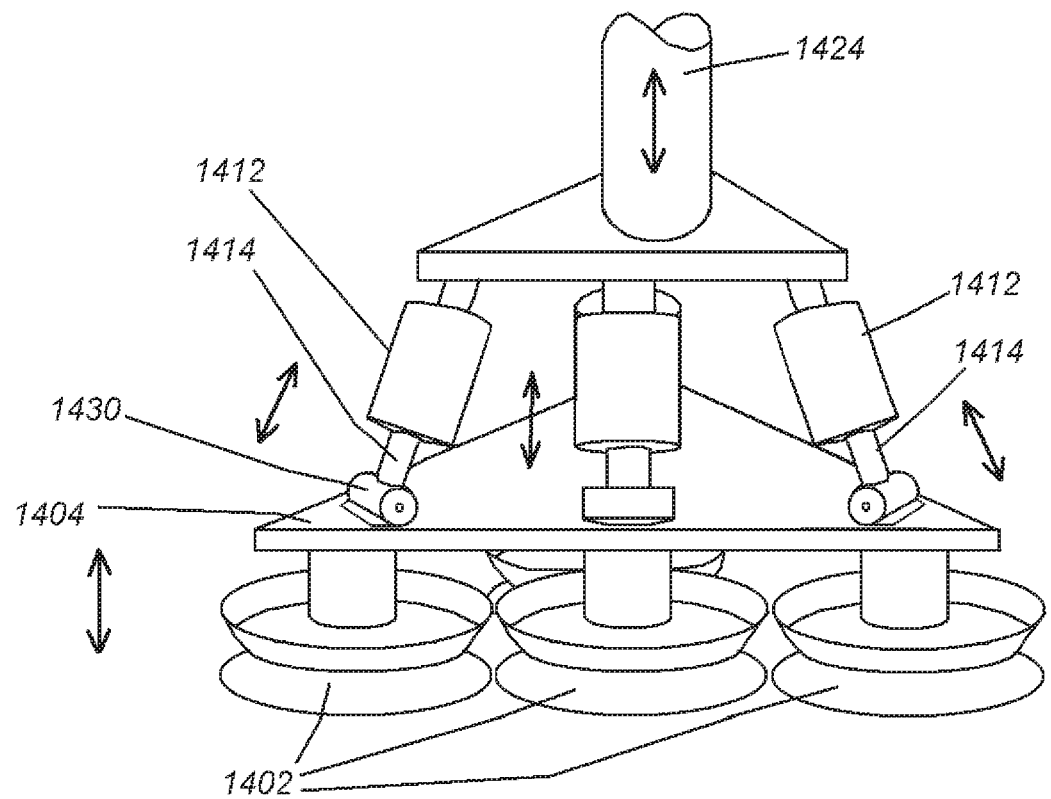
FIG. 14A is a perspective view of a mechanical CPR system with multiple CPR heads on a mounting plate, according to an illustrative embodiment.

FIG. 14A is a perspective view of a mechanical CPR system with multiple CPR heads on a mounting plate, according to an illustrative embodiment. A mechanical CPR system can have an upper piston 1424 that can provide compressive and/or decompressive force to the patient, and multiple CPR heads 1402 that can contact the patient and deliver the compressive and/or decompressive force from the upper piston 1424. The multiple CPR heads 1402 can be attached to a lower mounting plate 1404. Multiple lower actuators 1412 with lower pistons 1414 can be situated between the upper piston 1424 and the multiple CPR heads 1402. The lower actuators 1412 and lower pistons 1414 can allow the orientation of the lower mounting plate 1404 to be adjusted relative to the patient. For example, one or more corners of the plate can be higher or lower than other corners. The lower actuators 1412 and pistons 1414 can be hingedly connected between the upper piston 1424 and the lower mounting plate 1404 so that the orientation of the lower mounting plate can be adjusted by the lower actuators 1412 and pistons 1414.

Figure 14B:
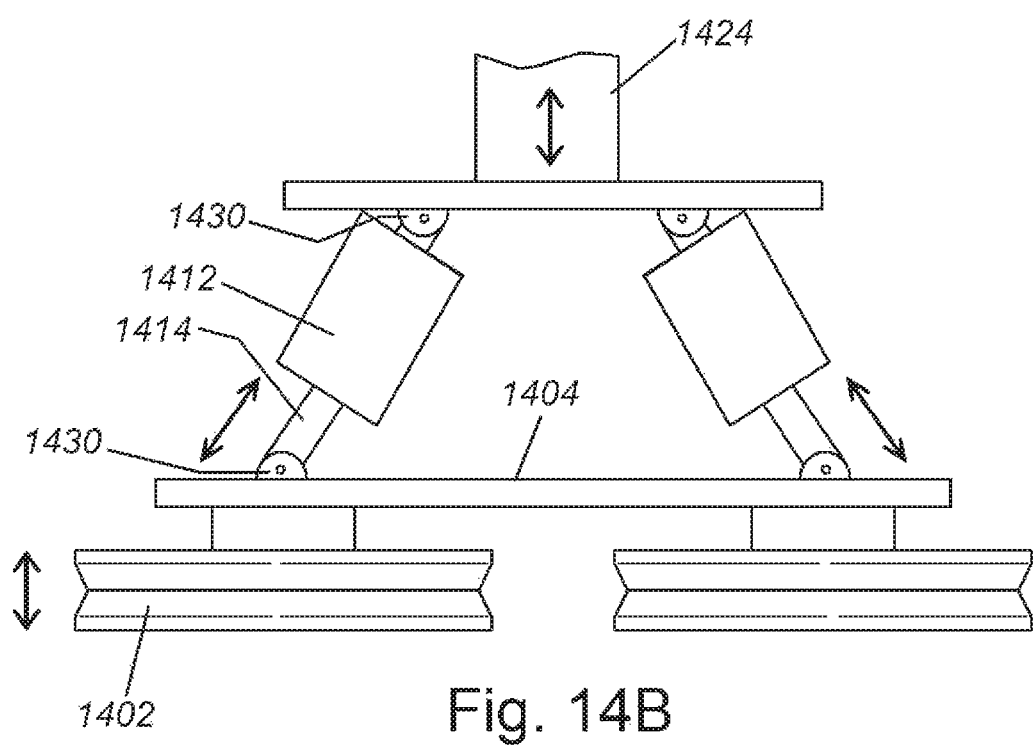
FIG. 14B is a side view of the mechanical CPR system with multiple CPR heads on a mounting plate of FIG. 14A, according to the illustrative embodiment.

FIG. 14B is a side view of the mechanical CPR system with multiple CPR heads on a mounting plate of FIG. 14A, according to the illustrative embodiment. Hinges 1430 can be located between the lower mounting plate 1404 and the lower actuators 1412 and pistons 1414, and hinges 1430 can be located between the upper piston 1424 and the lower actuators 1412 and pistons 1414.

Figure 15:
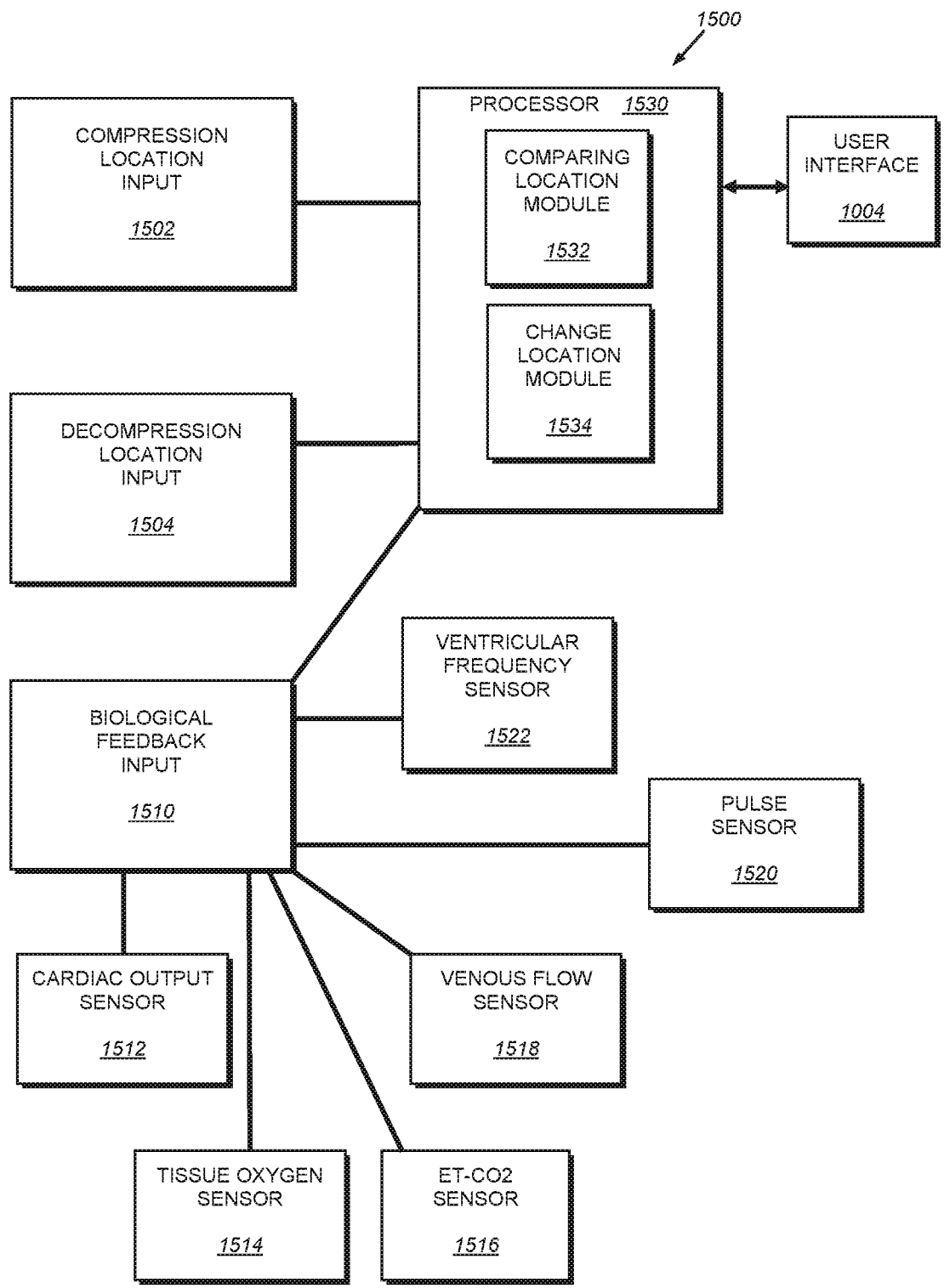
FIG. 15 is a diagram showing a system for monitoring and improving efficacy of varying compression locations, according to an illustrative embodiment.

FIG. 15 is a diagram showing a system for monitoring and improving efficacy of varying compression locations, according to an illustrative embodiment. The efficacy monitoring system 1500 for monitoring efficacy can include one or more compression location inputs 1502, one or more decompression location inputs 1504, and one or more biological feedback inputs 1510. Biological feedback input 1510 can receive measurements from biological system sensors that can include a cardiac output sensor 1512, a tissue oxygen sensor 1514, an ET-CO2 sensor 1516, venous flow sensor 1518, a pulse sensor 1520, and/or a ventricular fibrillation frequency sensor 1522.

The system 1500 can include a process(or) or module 1530 that can be operatively connected to a user interface such as user interface 1004. Processor 1530 can include a comparing process(or)/module 1532 and a change-location process(or)/module 1534. The comparing module 1532 can compare the biological feedback inputs from one or more biological sensors during compression at a first location to the biological feedback inputs from one or more biological sensors during compression at a second location, and can compare the biological feedback inputs measured during compression at the two locations to determine which of the two locations is the winner that has the most desirable measurements (i.e. the best location out of the two). The change-location module 1534 can select a new location to be compared to the winning location, and the change location module 1534 can direct the mechanical CPR system to change the location of compression to the new location. The comparing module 1532 can compare the biological feedback from the new location to the biological feedback from the previous winner location to determine the new winner location.

The comparing module 1532 can compare the biological feedback inputs from one or more biological sensors during decompression at a first location to the biological feedback inputs from one or more biological sensors during decompression at a second location, and can compare the biological feedback inputs measured during decompression at the two locations to determine which of the two locations is the winner that has the most desirable measurements (i.e. the best location out of the two). The change-location module 1534 can select a new location to be compared to the winning location, and the change location module 1534 can direct the mechanical CPR system to change the location of decompression to the new location. The comparing module 1532 can compare the biological feedback from the new location to the biological feedback from the previous winner location to determine the new winner location. Note that the above-described processes/ors and/or modules are exemplary of a variety of control and feedback architectures that can be implemented in various embodiments to perform the desired functions described herein. Alternate implementations should be clear to those of skill.

A method of providing personalized and customized CPR using the mechanical CPR system can include a multiple cycles of applying and releasing compression at a first location, and collecting feedback from one or more biological monitoring systems that can provide an indication of the efficacy of the compressions at the first location. The method can then include multiple cycles of applying and releasing compression at a second location, and collecting feedback from one or more biological monitoring systems that can provide an indication of the efficacy of the compressions at the second location. The method can include comparing the efficacy of the first location and the efficacy of the second location to determine the winner of the two locations. The method can include multiple cycles of applying and releasing compression at the winner location, and collecting feedback from one or more biological monitoring systems that can provide an indication of the efficacy of the compressions at the winner location. The method can include multiple cycles of applying and releasing compression at a third location, and collecting feedback from one or more biological monitoring systems that can provide an indication of the efficacy of the compressions at the third location. The method can include comparing the efficacy of the winner location and the efficacy of the third location to determine a new winner of the two locations. This method can continue to repeat with trying alternate locations, comparing the efficacy of the alternate location with the efficacy of the previous winner location, and determining a new winner location. Multiple cycles of applying and releasing compression can be used at the new winner location, and then compared with another alternate location. The number of cycles applied to winner locations and to alternate locations can be predetermined or can be variable based on the biological feedback.

A pumping cycle can include providing compression at one or more secondary locations that are different locations from the primary location of compression described above, so that a pumping action can be applied to the patient using multiple locations of compression. The multiple locations of compression can be applied in sequence throughout a compression cycle to create a pumping cycle. Hydraulic or pneumatic bladders can be used to provide a counterpulsing force to the patient to create a pumping cycle. Counterpulsing can include pushing on the abdomen at a different location and at different time in a compression cycle to improve the pumping of the blood.

The method of providing personalized and customized CPR using the mechanical system can include providing active decompression during the compression cycles. Active decompression can include use of a suction cup or adhesive to pull on the torso of the patient. The active decompression can be applied at the same location as the compression or at a different location on the patient.

The method of providing decompression can include a multiple cycles of applying and releasing decompression at a first location, and collecting feedback from one or more biological monitoring systems that can provide an indication of the efficacy of the decompression at the first location. The method can then include multiple cycles of applying and releasing decompression at a second location, and collecting feedback from one or more biological monitoring systems that can provide an indication of the efficacy of the decompression at the second location. The method can include comparing the efficacy of the decompression at the first location and the efficacy of the decompression at the second location to determine the winner of the two locations. The method can include multiple cycles of applying and releasing decompression at the winner location, and collecting feedback from one or more biological monitoring systems that can provide an indication of the efficacy of the compressions at the winner location. The method of providing decompression can include trying multiple types of decompression individually and/or in combination, including the use of suction decompression, the use of secondary location compression, and/or the use of bladders. The method can include trying various types of decompression and various locations of decompression in a play-the-winner format. Various combinations of compression locations, decompression locations, and decompression types can be combined and compared in a play-the-winner format.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, in various embodiments, compressive force can be provided through pneumatic or hydraulic bladders instead of pistons. Also, as used herein, various directional and orientational terms (and grammatical variations thereof) such as "vertical", "horizontal", "up", "down", "bottom", "top", "side", "front", "rear", "left", "right", "forward", "rearward", and the like, are used only as relative conventions and not as absolute orientations with respect to a fixed coordinate system, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances (e.g. 1-2%) of the system. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Accordingly, this description is meant to be taken only by way of example, and not to otherwise limit the scope of this invention.

What is claimed is:

1. A system for providing personalized Cardiopulmonary resuscitation (CPR) comprising:
   one or more pistons configured to provide a compressive force at a plurality of locations on a patient;
   one or more biological monitoring systems configured to measure feedback from one or more biological systems as the compressive force is applied at the plurality of locations on the patient; and
   a processor is configured to compare a first feedback as the compressive force is applied at a first location of the plurality of locations on the patient to a second feedback as the compressive force is applied at a second location of the plurality of locations on the patient.

2. The system of claim 1, further comprising one or more pistons configured to provide a decompressive force to the patient in sequence with the one or more pistons configured to provide the compressive force.

3. The system of claim 1, further comprising a compression belt configured to apply compression to the patient, and a rotary compression unit.

4. The system of claim 3, further comprising a rotary platform on the compression belt, wherein the rotary compression unit is mounted on the rotary platform.

5. The system of claim 1, further comprising a backboard and a frame, wherein the one or more pistons are mounted to the frame.

6. The system of claim 5, wherein the one or more pistons are pivotably mounted to the frame so that a force vector of the piston is capable of being adjusted.

7. The system of claim 1, wherein the processor is configured to compare the first and second feedbacks while the personalized CPR is being provided.

* * * * *